United States Patent [19]

Fertig, Sr.

[11] Patent Number: 4,849,636
[45] Date of Patent: Jul. 18, 1989

[54] ANALYZER WITH COMPENSATION

[75] Inventor: Glenn H. Fertig, Sr., Natrona Heights, Pa.

[73] Assignee: Mine Safety Appliances Company, Pittsburgh, Pa.

[21] Appl. No.: 195,715

[22] Filed: May 18, 1988

[51] Int. Cl.$^4$ ............................................. G01N 21/37
[52] U.S. Cl. .................................. 250/343; 250/252.1; 250/352
[58] Field of Search ................ 250/343, 344, 345, 352, 250/252.1

[56] References Cited

U.S. PATENT DOCUMENTS

| | | | |
|---|---|---|---|
| 4,110,619 | 8/1978 | Zörner | 250/344 |
| 4,423,739 | 1/1984 | Passaro et al. | 250/345 |
| 4,598,201 | 7/1986 | Fertig et al. | 250/343 |

OTHER PUBLICATIONS

Hill et al. "Cross-Sensitivity Effects in Non-Dispersive IR Gas Analyzers Using Condenser Microphone Detectors" J. Sci. Instrum. 1967 vol. 44, pp. 189–194.

Primary Examiner—Janice A. Howell
Assistant Examiner—Richard Hanig
Attorney, Agent, or Firm—Reed Smith Shaw & McClay

[57] ABSTRACT

The present invention pertains to an apparatus that is capable of correcting for inaccuracies caused by molecular collision broadening in analyzers. The apparatus includes an analyzer for analyzing a fluid. The analyzer is capable of producing an output signal corresponding to the fluid in the analyzer. The apparatus also includes a device for detecting molecular collision broadening in the fluid. The detecting device produces an output signal proportional to the molecular collision broadening. There is also a device for correcting inaccuracies in the analyzer output signal caused by molecular collision broadening. The correcting device is disposed to receive the analyzer output signal and the detecting device output signal, and is capable of producing an output signal corresponding thereto. Preferably, the detecting device includes a thermal conductivity cell and the correcting device is either a voltage control gain operational amplifier or a computer.

10 Claims, 4 Drawing Sheets

ANALYZER WITH COMPENSATION

FIELD OF THE INVENTION

The present invention relate to analyzers. More specifically, the present invention relates to a fluid analyzer that corrects for inaccuracies in the analyzer output signal caused by molecular collision broadening in the fluid.

BACKGROUND OF THE INVENTION

Inaccuracies caused by molecular collision broadening, manifest themselves as span effects. That is, the spectral-line shape identifying absorption of infrared radiation by a subject fluid is altered. This effect is described by Jamieson, McFee, Plass, Grube, and Richards in Infrared Physics and Engineering, 1963 published by McGraw-Hill, pages 32-37. The effect as it relates to anesthetic gases is described by D.L. Hill and T. Powell, J. Sci. Instrum., 1967 Vol. 44, pages 189-194.

In the course of development of an infrared analyzer to determine carbon dioxide in breath, this effect was prevalent when an anesthetic gas, for instance, nitrous oxide, was present. Nitrous oxide ($N_2O$) is the anesthetic gas of greatest concern because of the high concentrations used on a patient. As great a concentration as 80% nitrous oxide in oxygen is used.

When, for example, a typical infrared analyzer is calibrated on 10% carbon dioxide in air, and the nitrogen present is replaced with nitrous oxide, collision broadening of the carbon dioxide molecule takes place. That is, if 10% carbon dioxide in 10% oxygen and 80% nitrous oxide is passed through the analyzer, the analyzer only reads 9.5% carbon dioxide, as shown in FIG. 5. This effect is most prevalent in highly selective analyzers. These analyzers are of the type described by Hill, or further described in U.S. Pat. No. 4,598,201 to Fertig, et al. The effect also is manifested in analyzers having highly selective infrared sources such as laser sources where discrete lines of energy coincide with the absorption lines of the fluid of interest, or the selective type sources described in U.S. Pat. No. 2,212,211 to Pfund.

SUMMARY OF THE INVENTION

The present invention pertains to an apparatus that is capable of correcting for inaccuracies caused by molecular collision broadening in analyzers. The apparatus comprises an analyzer for analyzing a fluid. The analyzer is capable of producing an output signal corresponding to the fluid in the analyzer. The apparatus also comprises means for detecting molecular collision broadening in the fluid. The detecting means produces an output signal proportional to the molecular collision broadening. There is also means for correcting inaccuracies in the analyzer output signal caused by molecular collision broadening. The correcting means is disposed to receive the analyzer output signal and the detecting means output signal, and is capable of producing an output signal corresponding thereto.

In a preferred embodiment, the detecting means includes means for determining molecular collision broadening in the fluid by determining the thermal conductivity of the fluid in the analyzer and producing an output signal proportional to the molecular collision broadening resulting from the presence of the interfering gas. There is also means for correcting inaccuracies in the analyzer output signal caused by molecular collision broadening. The correcting means is disposed to receive the analyzer output signal and the determining means output signal and adjust the relative magnitude of the signals to apply the proper correction to the analyzer output signal.

In an even more preferred embodiment, the determining means includes a thermal conductivity cell or other device giving an output responsive to an interfering gas concentration and the correcting means is either a voltage control gain operational amplifier or a computer operative on the determining means output signal.

Other details, objects and advantages of the invention will become apparent as the following description of the presently preferred embodiments and presently preferred methods of practicing the invention proceeds.

BRIEF DESCRIPTION OF THE DRAWINGS

In the accompanying drawings, preferred embodiments of the invention and preferred methods of practicing the invention are illustrated, in which.

DESCRIPTION OF THE PREFERRED EMBODIMENT

Figure 1:
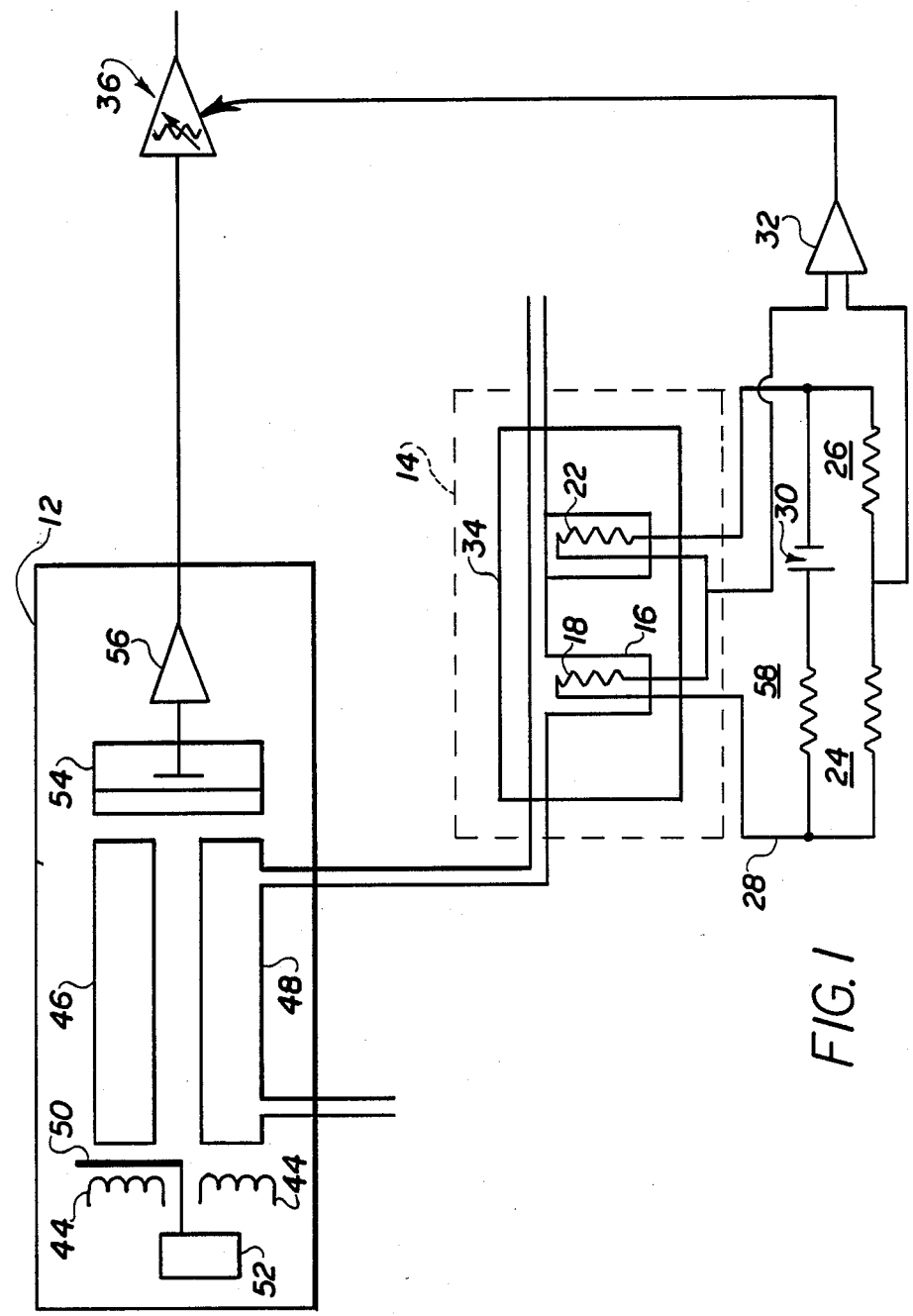
FIG. 1 is a schematic representation of an apparatus that is capable of correcting for inaccuracies due to molecular collision broadening.

Referring now the drawings, wherein like reference numerals designate identical or corresponding parts throughout the several views, and more particularly to FIG. 1 thereof, there is shown an apparatus 10 that is capable of correcting for inaccuracies due to molecular collision broadening in a fluid under analysis. The apparatus 10 comprises an analyzer 12 for analyzing a fluid. The analyzer 12, preferably an infrared analyzer 12, is capable of producing an output signal corresponding to the fluid in the analyzer 12. The apparatus 10 also comprises means for detecting molecular collision broadening in the fluid. The detecting means is capable of producing an output signal proportional to the molecular collision broadening. There is also means for correcting inaccuracies in the analyzer 10 output signal caused by molecular collision broadening. The correcting means is disposed to receive the analyzer output signal and the detecting means output signal, and is capable of producing an output signal corresponding thereto.

The detecting means can include means for determining molecular collision broadening in the fluid by determining the thermal conductivity of the fluid in the analyzer. The determining means produces an output signal proportional to the molecular collision broadening in the fluid. The connecting means is then disposed to receive the analyzer output signal and the determining means output signal. The correcting means adjusts the relative magnitude of the analyzer output signal to apply the proper correction to the analyzer output signal.

The determining means preferably includes a thermal conductivity cell 14. The thermal conductivity cell 14 is fluidically connected to the analyzer 12 such that fluid analyzed by the analyzer 12 is received by the thermal conductivity cell 14. The thermal conductivity cell 14 is capable of producing an output signal corresponding to the molecular collision broadening present in the fluid.

The thermal conductivity cell 14 preferably includes a sample cavity 16 that is disposed to receive fluid from the infrared analyzer 12. A sample resistive element 18 is disposed in the sample cavity 16. The sample resistive element 18 is capable of providing heat to the fluid in the sample cavity 16 at a rate dependent upon the thermal conductivity of the fluid.

The thermal conductivity cell 14 also includes a reference cavity 20 which is sealed. A reference fluid is in the reference cavity 20. The reference fluid is known and of a constant composition. A reference resistive element 22 is disposed in the reference cavity 20. The reference resistive element 22 is capable of providing heat to the reference fluid in the reference cavity 20 at a rate dependent upon the thermal conductivity of the reference fluid.

The thermal conductivity cell 14 further includes a third resistive element 24 and a fourth resistive element 26. The third resistive element 24 and the fourth resistive element 26 are electrically connected to the sample resistive element 18 and the reference resistive element 22 such that these resistive elements form a wheatstone bridge circuit 28. A voltage source 30 can be electrically connected to the wheatstone bridge circuit 28 in order to supply current thereto.

The thermal conductivity cell 14 preferably also includes the differential amplifier 32. The differential amplifier 32 is electrically connected to the wheatstone bridge circuit 28 such that the differential amplifier 32 prodcues an output signal corresponding to the molecular collision broadening present in the fluid. The sample cavity 16 and the reference cavity 20 are preferably contained in a metal block 34. The sample cavity 16 and the reference cavity 20 are preferably heated to a constant temperature by the metal block 34. Preferably, the sample resistive element 18 and the reference resistive element 22 are each self-heating thermistors.

The connecting means preferably includes a voltage controlled gain operational amplifier 36. The infrared analyzer 12 is electrically connected to the voltage controlled gain operational amplifier 36 such that the infrared analyzer output signal is capable of being received by the operational amplifier 36. Also, the differential amplifier 32 is electrically connected to the voltage controlled gain operational amplifier 36 such that the differential amplifier 32 output signal is capable of being received by the operational amplifier 36 and controlling the gain thereof. The voltage controlled gain operational amplifier 36 is capable of producing an output signal proportional to the infrared analyzer 12 output signal and the differential amplifier 32 output signal.

Figure 2:
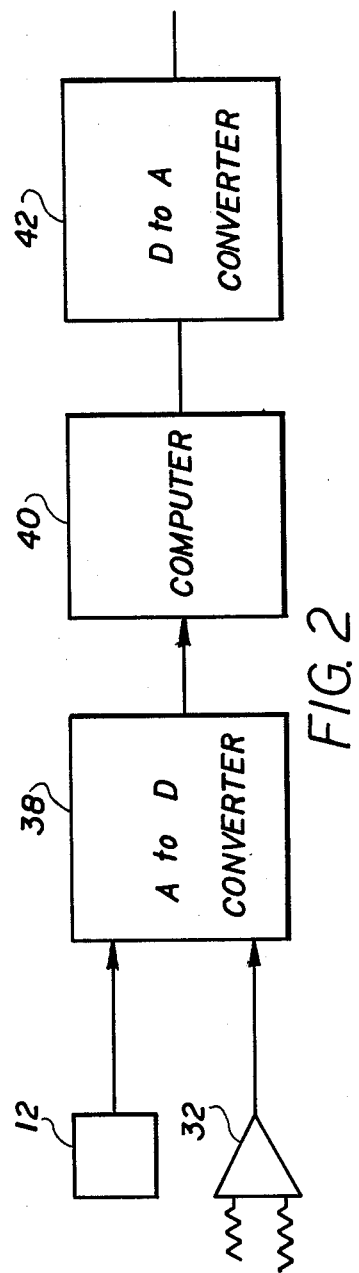
FIG. 2 is a schematic diagram of a computer, an A to D, and a D to A convertor.

Alternatively, and referring to FIG. 2, the connecting means can include an A to D convertor 38 that is electrically connected to the infrared analyzer 12 and the differential amplifier 32 such that the A to D convertor 38 is capable of receiving the output signal of the infrared analyzer 12 and the output signal of the differential amplifier 32 and producing a digital output signal corresponding thereto. In the alternative embodiment, the connecting means also includes a computer 40 that is electrically connected to the A to D convertor 38 such that the computer is capable of receiving the digital output signal of the A to D convertor 38 and producing an output signal that is compensated for molecular collision broadening in the fluid. There is also a digital to analog convertor 42 which is electrically connected to the computer such that the digital to analog convertor 42 is capable of receiving the computer output signal and producing an analog output signal corresponding to the computer 40 output signal.

In the operation of a preferred embodiment, where the apparatus 10 is used for the analysis of fluid containing the anesthetic gas nitrous oxide, the infrared analyzer 12 is of a type similar to that described in U.S. Pat. No. 4,598,201 to Fertig, et al. Briefly, such an infrared analyzer 12 has an infrared source 44 that provides the infrared radiation to a reference cell 46 and a sample cell 48. The reference cell 46 contains a known fluid that does not absorb infrared radiation energy that the fluid passing through the sample cell 48 absorbs. The infrared radiation passes through the reference cell 46 and sample cell 48 alternately, due to an interrupter 50 powered by a motor 52, and is received by an infrared detector 54. The infrared detector 54 produces a signal corresponding to the fluid in the sample cell 48. The signal produced by the infrared detector 54 is amplified by an amplifier 56. The output signal of the infrared analyzer 12 is calibrated for 0% to 10% $CO_2$ in air. That is, when 100% $CO_2$ free air is placed into the sample cell 48, the output signal of the infrared analyzer 12 is 0. Then, with 10% $CO_2$ in air present in the sample cell 48, the output signal of the infrared analyzer 12 represents 100% of full scale.

The fluid in the sample cell 48 flows to the sample cavity 16 of the thermal conductivity cell 14. This sample cavity 16 is contained in a metal block 34. The metal block 34 is heated to a constant temperature. In the sample cavity 16, heat is lost from the sample resistive element 18 at a rate dependent upon the thermal conductivity of the fluid in the sample cavity 16. This heat loss affects the resistance of the sample resistive element 18, causing a change in the voltage across the sample resistive element 18. Similarly, reference resistive element 22 in reference cavity 20, which is also in the metal block 34, loses heat at a rate dependent upon the thermal conductivity of the known fluid in the reference cavity 20. This known fluid can be, for instance, 80% nitrous oxide. Since the property of thermal conductivity is associated with the transfer of kinetic energy due to a temperature gradient, the thermal conductivity of a fluid corresponds to the molecular collision broadening present in a fluid.

The voltages present across the sample resistive element 18 and the reference resistive element 22 affect the voltage of the wheatstone bridge circuit 28, of which they are a part. Operation of a wheatstone bridge circuit 28 is well known. The wheatstone bridge circuit 28 is powered by a voltage source 20. The current from the voltage source can be limited by a current limiting resistor 58 that prevents thermal runaway and burnout of the sample resistive element 18 and the reference resistive element 22.

Figure 3:
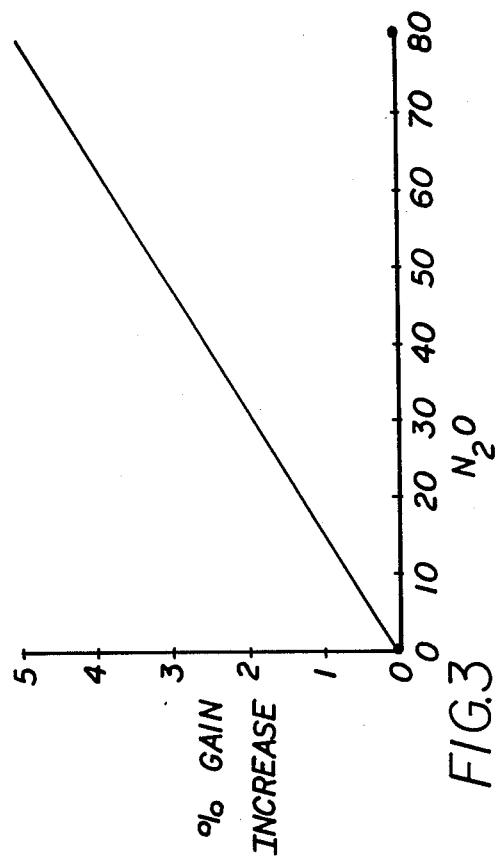
FIG. 3 is a graph of the output voltage of the differential amplifier as a function of percentage of $N_2O$ in air.

The wheatstone bridge circuit 28 is electrically connected to differential amplifier 32. Differential amplifier 32 produces a signal corresponding only to the difference in the voltage across the sample resistive element 18 and the reference resistive element 22. The gain of the differential amplifier 32 is adjusted so that its output signal is equal to one volt with 80% $N_2O$ present in the fluid, as shown in FIG. 3. The output signal from the infrared analyzer 12 and the differential amplifier 32 can be connected to one of two types of circuits.

Figure 4:
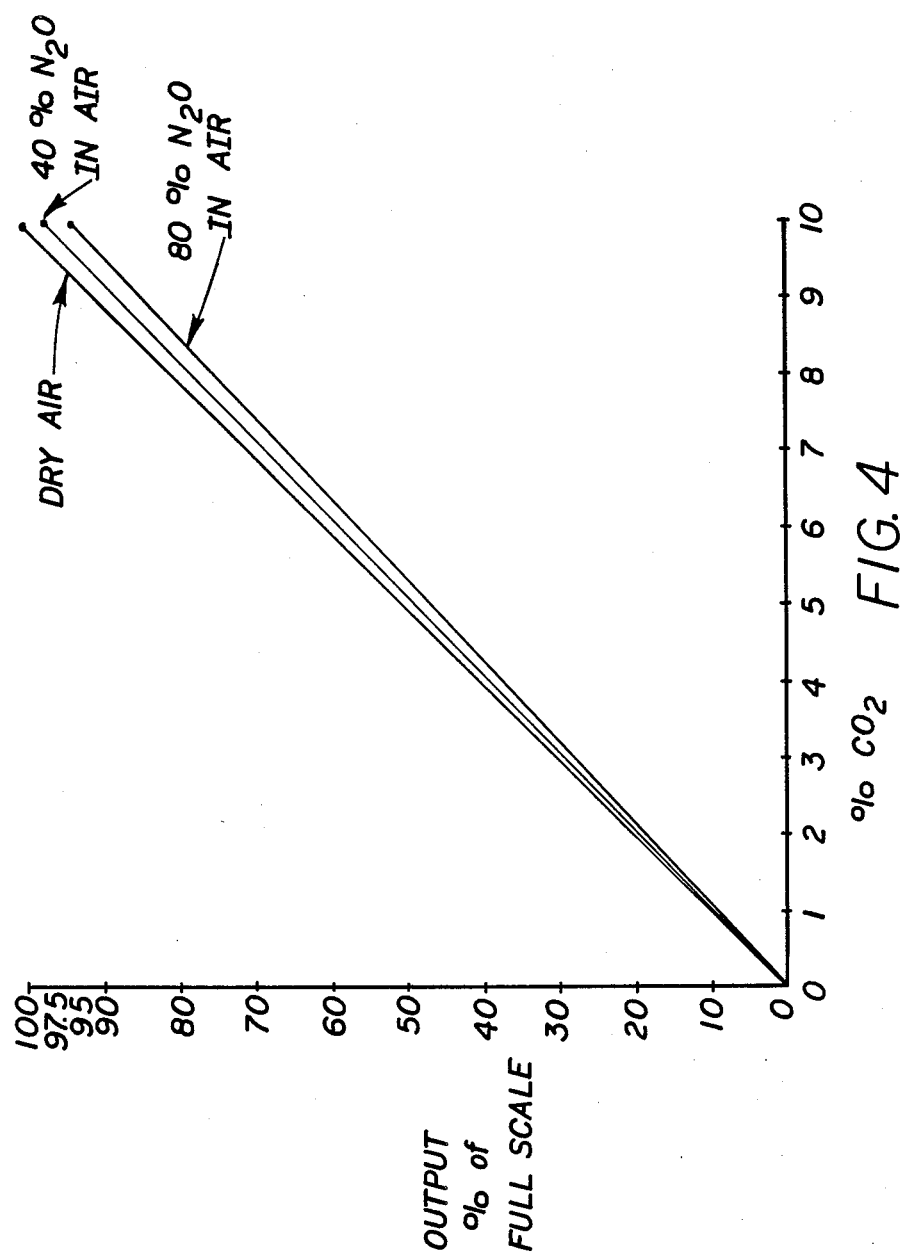
FIG. 4 is a graph of the percent gain increase as a function of the percent of $N_2O$ in the fluid.

If an analog system is desired to be used, the output signal from the infrared analyzer 12 is received by the operational amplifier 36. The gain of the operational amplifier 36 is controlled by the output signal from the differential amplifier 32. The percent gain increase in the operational amplifier 36 as a function of N₂O present in the fluid is shown in FIG. 4.

Alternatively, if a computer 40 is utilized, the output signal from the infrared analyzer 12 and the output signal from the differential amplifier 32 are received by the analog to digital convertor 38 which digitizes them. The digitized signals from the analog to digital converter 38 are received by the computer 40. In the computer 40, the following calculation takes place.

$$O = (Ir) + (Tc \cdot X)$$

where:
- O = corrected output signal
- Ir = signal from infrared analyzer
- Tc = N₂O calibrated output from the thermal conductivity cell normalized to ten, full range.
- X = percent effect of molecular collision broadening on infrared analyzer span.

(Note that this equation, while specific for the preferred embodiment discussed herein, is general in that it is applicable for any fluid under analysis and any calibration and normalization range). The corrected digital output signal from the computer 24 is received by a digital to analog converter 42 which provides a corrected analog signal.

Figure 5:
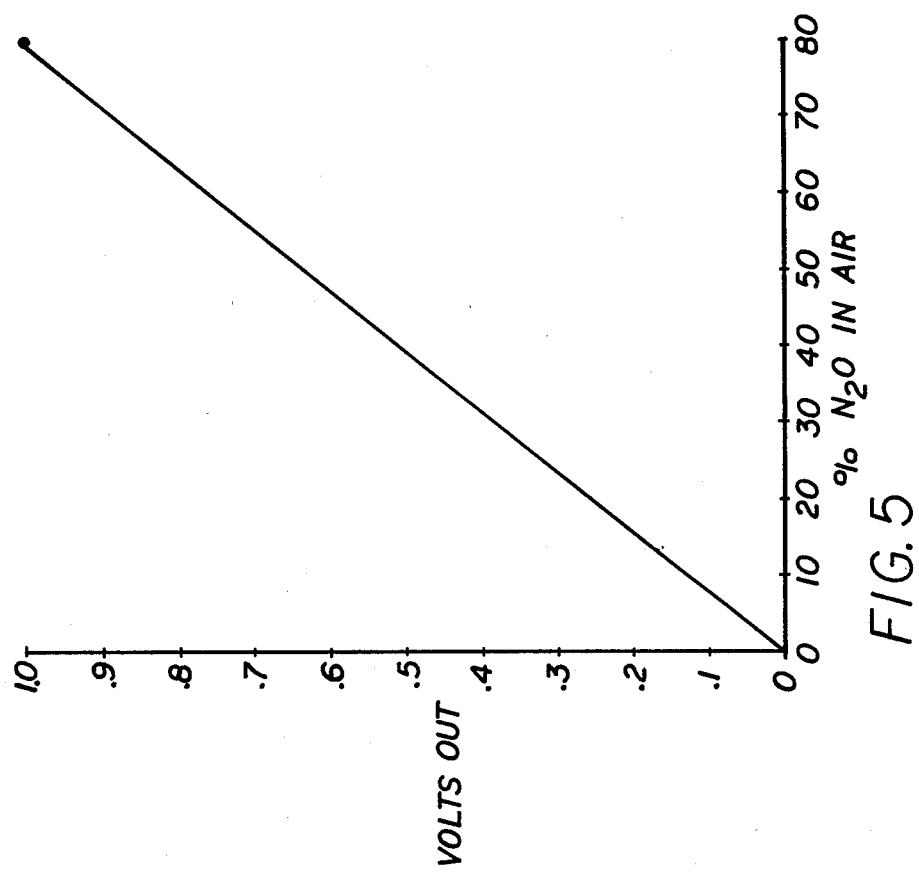
FIG. 5 is a graph of the output percent of full scale as a function of the percentage of $CO_2$ copmrised of either dry air, 40% of $N_2O$ in air, or 80% of $N_2O$ in air.

The resulting compensated output signal from either the digital to analog converter 42 or the operational amplifier 36 has removed therefrom inaccuracies due to molecular collision broadening in the fluid. Thus, the errors depicted by FIG. 5 when 40% N₂O in air or 80% N₂O in air is present are essentially removed.

Although the invention has been described in detail in the foregoing embodiments for the purpose of illustration, it is to be understood that such detail is solely for that purpose and that variations can be made therein by those skilled in the art without departing from the spirit and scope of the invention except as it may be described in the following claims. Those skilled in the art will recognize that means for determining molecular collision broadening may incorporate any conventional gas analyzer appropriate to the interferring gas to be determined, such as, for example, catalytic, that uses instruments for combustible gases and electromechanical sensors for a variety of toxic gases.

What is claimed is:

1. An apparatus comprising:
   an analyzer for analyzing a fluid, said analyzer capable of producing an output signal corresponding to the fluid in the analyzer;
   means for detecting molecular collision broadening in the fluid, said detecting means is capable of producing an output signal proportional to the molecular collision broadening; and
   means for correcting inaccuracies in the analyzer output signal caused by molecular collision broadening, said correcting means disposed to receive the analyzer output signal and the detecting means output signal, and capable of producing an output signal corresponding thereto.

2. An apparatus as described in claim 1 wherein the detecting means includes means for determining molecular collision broadening in the fluid by determining the thermal conductivity of the fluid in the analyzer and producing an output signal proportional to the molecular collision broadening in the fluid.

3. An apparatus as described in claim 2 wherein the correcting means is disposed to receive the analyzer output signal and the determining means output signal and adjust the relative magnitude of the analyzer output signal to apply the proper correction to the analyzer output signal.

4. An apparatus as described in claim 3 wherein the determining means includes a thermal conductivity cell fluidically connected to the analyzer such that fluid analyzed by the analyzer is received by the thermal conductivity cell, said thermal conductivity cell being capable of producing an output signal corresponding to the molecular collision broadening present in the fluid.

5. An apparatus as described in claim 4 wherein the analyzer is an infrared analyzer.

6. An apparatus as described in claim 5 wherein
   the thermal conductivity cell includes a sample cavity disposed to receive fluid from the infrared analyzer;
   a sample resistive element disposed in the sample cavity which is capable of providing heat to the fluid in the sample cavity at a rate dependent upon the thermal conductivity of the fluid;
   a reference cavity which is sealed;
   a reference fluid in the reference cavity, said reference fluid being known and of a constant composition;
   a reference resistive element disposed in the reference cavity which is capable of providing heat to the reference fluid in the reference cavity at a rate dependent upon the thermal conductivity of the reference fluid;
   a third resistive element and a fourth resistive element electrically connected to the sample resistive element and the reference resistive element such that the sample, reference, third and fourth resistive elements form a wheatstone bridge circuit;
   a voltage source electrically connected to the wheatstone bridge circuit for supplying current thereto; and
   a differential amplifier electrically connected to the wheatstone bridge circuit such that the differential amplifier produces an output signal corresponding to the molecular collision broadening present in the fluid.

7. An apparatus as described in claim 6 wherein the correcting means includes a voltage controlled gain operational amplifier, said infrared analyzer being electrically connected to the voltage controlled gain operational amplifier such that the infrared analyzer output signal is capable of being received by the operational amplifier, and said differential amplifier being electrically connected to the voltage controlled gain operational amplifier such that the differential amplifier output signal is capable of being received by the operational amplifier and controlling the gain thereof, said operational amplifier is capable of producing an output signal proportional to the infrared analyzer output signal and the differential amplifier output signal.

8. An apparatus as described in claim 6 wherein
   the connecting means includes an A to D converter that is electrically connected to the infrared analyzer and the differential amplifier such that the A to D convertor is capable of receiving the output signal of the infrared analyzer and the output signal of the differential amplifier and producing a digital output signal corresponding thereto;

a computer that is electrically connected to the A to D convertor such that the computer is capable of receiving the digital output signal of the A to D converter and producing an output signal that is compensated for molecular collision broadening in the fluid; and a digital to analog converter which is electrically connected to the computer such that the digital to analog converter is capable of receiving the computer output signal and producing an analog output signal corresponding to the computer output signal.

9. An apparatus as described in claim 7 or 8 wherein the sample cavity and the reference cavity are contained in a metal block and are heated to a constant temperature.

10. An apparatus as described in claim 9 wherein the sample resistive element is a self-heated thermistor and the reference resistor element is a self-heated thermistor.

* * * * *